United States Patent
Goodnough

(10) Patent No.: US 11,351,476 B2
(45) Date of Patent: Jun. 7, 2022

(54) METHOD FOR CHEMICAL SEPARATION OF CANNABINOIDS

(71) Applicant: AGRIFY CORPORATION, Billerica, MA (US)

(72) Inventor: Alex Goodnough, Ferndale, MI (US)

(73) Assignee: AGRIFY CORPORATION, Billerica, MA (US)

(*) Notice: Subject to any disclaimer, the term of this patent is extended or adjusted under 35 U.S.C. 154(b) by 249 days.

(21) Appl. No.: 16/781,330

(22) Filed: Feb. 4, 2020

(65) Prior Publication Data

US 2021/0205732 A1 Jul. 8, 2021

Related U.S. Application Data

(60) Provisional application No. 62/957,902, filed on Jan. 7, 2020.

(51) Int. Cl.

| | |
|---|---|
| C07C 65/00 | (2006.01) |
| C07C 51/00 | (2006.01) |
| B01D 11/00 | (2006.01) |
| B01D 11/04 | (2006.01) |
| C07D 311/80 | (2006.01) |
| C07C 65/17 | (2006.01) |
| C07C 51/573 | (2006.01) |

(52) U.S. Cl.
CPC .......... *B01D 11/0492* (2013.01); *C07C 65/17* (2013.01); *C07D 311/80* (2013.01); *C07C 51/573* (2013.01)

(58) Field of Classification Search
CPC ...... B01D 11/0492; C07C 65/14; C07C 51/00
See application file for complete search history.

(56) References Cited

U.S. PATENT DOCUMENTS

| | | |
|---|---|---|
| 7,344,736 B2 | 3/2008 | Whittle et al. |
| 9,034,395 B2 | 5/2015 | Whittle et al. |
| 2014/0248379 A1 | 9/2014 | Mueller |
| 2015/0044315 A1 | 2/2015 | Letzel et al. |
| 2016/0106705 A1 | 4/2016 | Verzura et al. |
| 2016/0346339 A1 | 12/2016 | Finley et al. |
| 2019/0038663 A1 | 2/2019 | Kotra et al. |

*Primary Examiner* — Sikarl A Witherspoon
(74) *Attorney, Agent, or Firm* — Carlson, Gaskey & Olds, P.C.

(57) ABSTRACT

A method for chemical separation of cannabinoids includes: (i) providing a starting organic solvent solution that contains a mixture of cannabinoid acids, (ii) using an aqueous basic solution to remove a portion of the cannabinoid acids from the mixture of cannabinoid acids in the starting organic solvent solution by converting the portion of the cannabinoid acids to cannabinoid carboxylate salts that solubilize in the an aqueous basic solution, (iii) separating the aqueous basic solution in (ii) from the starting organic solvent, (iv) combining the aqueous solution from (iii) with new organic solvent to produce a combined solution, (v) acidifying the combined solution to extract the cannabinoid acids from the aqueous solution to the organic solvent, (vi) separating the organic solvent of (v) from the aqueous solution, and (vii) evaporating the organic solvent of (vi) to leave product cannabinoid acids.

20 Claims, No Drawings

METHOD FOR CHEMICAL SEPARATION OF CANNABINOIDS

CROSS-REFERENCE TO RELATED APPLICATION

This application claims priority to U.S. Provisional Application No. 62/957,902 filed Jan. 7, 2020.

BACKGROUND

A known method for producing cannabis extracts with a concentration of tetrahydrocannabinolic acid (THCA) and tetrahydrocannabinol (THC) below 0.3% involves diluting the extract with a non-cannabinoid material, such as medium chain triglycerides, propylene glycol, or other high-boiling point diluents. Such diluents, however, typically cannot be readily separated from the cannabinoid mixture, thereby diminishing the value of the extract. Another option is diluting with purified cannabinoids other than THC or THCA, but many such cannabinoids are solids in pure form and thus make for poor diluents.

Solid-liquid chromatography is another method for the removal of THC and THCA from cannabinoid extracts. The solid-liquid chromatography separates cannabinoids in the extract. All fractions are then recombined except those containing THC and/or THCA to yield a product that is low in THC and/or THCA. Although useful, solid-liquid chromatography has low throughput, is solvent intensive, and may require expensive adsorbents that are not easily regenerated.

SUMMARY

A method for chemical separation of cannabinoids according to an example of the present disclosure includes step (i) of providing a starting organic solvent solution that contains a mixture of cannabinoid acids; step (ii) of using an aqueous basic solution to remove a portion of the cannabinoid acids from the mixture of cannabinoid acids in the starting organic solvent solution by converting the portion of the cannabinoid acids to cannabinoid carboxylate salts that solubilize in the aqueous basic solution.; step (iii) of separating the aqueous basic solution in step (ii) from the starting organic solvent; step (iv) of combining the aqueous solution from step (iii) with new organic solvent to produce a combined solution; step (v) of acidifying the combined solution to extract the cannabinoid acids from the aqueous solution to the organic solvent; step (vi) of separating the organic solvent of step (v) from the aqueous solution; and step (vii) of evaporating the organic solvent of step (vi) to leave product cannabinoid acids.

A method for chemical separation of cannabinoids according to an example of the present disclosure includes providing a starting cannabis material that contains cannabinoids, including, by weight, a concentration of more than 0.3% of total tetrahydrocannabinol, followed by step (i) of combining the starting cannabis material with an organic solvent to produce a starting organic solvent solution that contains the cannabinoid acids; step (ii) of using an aqueous basic solution to remove a portion of the cannabinoid acids from the starting organic solvent solution by converting the cannabinoid acids to cannabinoid carboxylate salts that solubilize in the an aqueous basic solution; step (iii) of separating the aqueous basic solution in step (ii) from the starting organic solvent solution, the separated aqueous basic solution having a lower concentration of total tetrahydrocannabinol than the starting cannabis material; step (iv) of combining the aqueous basic solution of step (iii) with fresh organic solvent to remove a portion of the cannabinoid acids from the aqueous basic solution, and separating the aqueous basic solution in from the organic solvent, the separated aqueous basic solution having a lower concentration of total tetrahydrocannabinol than the aqueous basic solution of step (iii), and combining the separated aqueous solution from with fresh organic solvent to form a combined solution; step (v) of acidifying the combined solution to extract cannabinoid acids from the aqueous solution to the organic solvent; step (vi) of separating the organic solvent of step (v) from the aqueous solution; and step (vii) of evaporating the organic solvent of step (vi) to leave a purified form of the cannabinoid acids, the purified form having, by weight, a greater concentration of the total tetrahydrocannabinol than the starting cannabis material.

DETAILED DESCRIPTION

The present disclosure relates to a methodology for separation of cannabinoids, such as tetrahydrocannabinolic acid (THCA) and tetrahydrocannabinol (THC), from cannabis extracts that contain cannabinoid acids such as THCA and cannabidiolic acid (CBDA), and especially those that are rich in CBDA. For example, the extract may be a solvent-based extract that contains a concentration, by weight, of total THC that is greater than 0.3%. Total THC refers to the total amount of THC accounting for the conversion of THCA into THC consistent with 7 C.F.R Part 990. In particular, the method may be used to obtain a purified form, product, or extract that is enriched in CBDA and which in some instance also contains a concentration of total THC of less than 0.3%, without dilution of the concentration of other cannabinoids such as CBDA.

The methodology generally involves a liquid-liquid extraction in which cannabinoid acids are converted to cannabinoid carboxylate salts, which are solubilized in water. The resulting aqueous solution may then be combined with an organic solvent, which may be a mixture of several solvents of differing polarities. An example includes a mixture of hexane and ethyl acetate. "Hexane" as used herein encompasses n-hexane, mixtures of n-hexane and one or more hexane isomers, or mixtures of two or more hexane isomers. The solution is then acidified and a purified mixture of cannabinoids is extracted from the acidified solution.

An example or examples of the disclosed method are described herein with regard to functions and/or actions that are numerically designated. Although the numerical designations indicate the order in which the functions and/or actions are generally conducted, such designations do not necessarily preclude the use of the method with other intervening functions and/or actions.

In one example, the method initially includes a step (i) of providing a starting organic solvent solution that contains a mixture of cannabinoid acids. This starting organic solvent solution may be provided as a pre-prepared solution, but alternatively may be prepared via known techniques for extraction of cannabis plant material. In one example, the starting organic solvent solution includes an organic solvent and a crude cannabis oil that contains the mixture of cannabinoid acids. For instance, the crude cannabis oil contains, by weight, a concentration of greater than 0.3% of THCA and a concentration of CBDA that is greater than the concentration of THCA, such as greater by a factor of 2, a factor of 5, or a factor of 14. The organic solvent may include a non-polar solvent, such as hexane, that is combined with the crude cannabis oil. In one example, the organic solvent also includes a polar solvent, such as ethyl acetate. Most typically, the organic solvent will include, by volume, substantially less of the polar solvent than the non-polar solvent. Agitation, such as sonication, may be used to homogenize the solution.

The method then includes step (ii) of using an aqueous basic solution to remove a portion of the cannabinoid acids (e.g., CBDA) from the mixture of cannabinoid acids in the starting organic solvent solution by converting the portion of the cannabinoid acids to cannabinoid carboxylate salts that solubilize in the an aqueous basic solution. For example, the aqueous basic solution is an aqueous sodium hydroxide. In one further example, the aqueous sodium hydroxide is a 1 M solution of sodium hydroxide.

In step (iii), the aqueous basic solution of step (ii) is separated from the starting organic solvent. For example, the separation is conducted using a separatory funnel, the operation of which is well known and thus not discussed further herein. Steps (ii) and (iii) may in essence be combined by transferring the starting organic solvent solution to the separatory funnel and then adding the aqueous basic solution, i.e. washing the organic solvent solution with the aqueous basic solution.

In step (iv), the aqueous solution from step (iii) is combined with fresh organic solvent to produce a combined solution. For example, the organic solvent may be of the same composition as the organic solvent used in step (i). For instance, the organic solvent is hexane or is a mixture of a non-polar solvent, such as hexane, and a polar solvent, such as ethyl acetate. For a mixture, another separation may be conducted, followed by another combining step with a fresh organic solvent, such as hexane.

In step (v), the combined solution is acidified to extract the cannabinoid acids from the aqueous solution into the organic solvent. As an example, the acidifying is conducted by adding an acid to the combined solution until the pH of the combined solution reaches a designated level, such as below a pH of 5, but more typically below a pH of 4 or pH of 2. In one example, the acid is hydrochloric acid. The combined solution or the aqueous solution prior to combining, may be chilled to a temperature substantially below room temperature, such as 0° C., and agitated by stirring or the like. The acidifying is exothermic and the chilling may thus facilitate maintaining temperature control.

In step (vi), the organic solvent of step (v) is then separated from the aqueous solution. For instance, as above, a separatory funnel may be used for the separation.

In step (vii), the organic solvent of step (vi) is evaporated to leave byproduct cannabinoid acids. Prior to evaporation, the organic solvent from step (vi) may be desiccated to remove acid and filtered. For example, the resulting byproduct has, by weight, a concentration of less than 0.3% of tetrahydrocannabinolic acid (THCA) and a concentration of at least 80% of cannabidiolic acid (CBDA).

The following examples demonstrate additional aspects of the method.

Example 1

To a tared beaker was added $CO_2$ extracted crude oil (7.219 g, 68% CBDA, 5% THCA) and hexane (36.74 mL). The mixture was sonicated until a homogenous solution formed, at which point ethyl acetate (1.84 mL) was added. The solution was transferred to a separatory funnel and washed with aqueous 1 M NaOH (1×50 mL). The layers were separated, and the aqueous phase transferred to a clean separatory funnel and washed with 5% ethyl acetate in hexane (1×50 mL). The layers were separated, and the aqueous phase was cooled to 0° C. with stirring before adding hexane (50 mL) and increasing the stir speed until the biphasic mixture emulsified. To the stirred, cooled emulsion was added HCl (36.5-38%) in 5 mL portions until the pH of the mixture was about 2 by litmus paper. The acidified mixture was transferred to a separatory funnel and the layers were separated. The organic layer was rested over solid $NaHCO_3$ desiccant for 5 minutes before filtering the solution and removing the solvent under reduced pressure to yield an off-white foam product having a mass of 4.47 g and containing a concentration, by weight, of 85.5% CBDA and 0.28% THCA, representing a 77% recovery of CBDA. The byproduct collapsed into an oil when warmed.

Example 2

To a tared Erlenmeyer flask was added ground hemp (36.8 g, 10.02% CBDA, 0.33% total THC) followed by hexane (250 mL). The mixture was stirred vigorously for 15 minutes at room temperature and then filtered through 8 um filter paper to yield an amber miscella (140 mL). After adding ethyl acetate (7 mL, 5% v/v) to the miscella the solution was transferred to a separatory funnel and washed with aqueous 1 M NaOH (1×300 mL). The layers were separated, and the aqueous phase transferred to a clean separatory funnel and washed with 5% ethyl acetate in hexanes (1×300 mL). The layers were separated, and the aqueous phase was cooled to 0° C. with stirring before adding hexane (300 mL) and increasing the stir speed until the biphasic mixture emulsified. To the stirred, cooled emulsion was added HCl (36.5-38% w/w) in 5 mL portions until the pH of the mixture was about 2 by litmus paper. The acidified mixture was transferred to a separatory funnel and the layers were separated. The organic layer was rested over solid $NaHCO_3$ desiccant for 5 minutes before filtering the solution and removing the solvent under reduced pressure to yield an off-white foam product having a mass of 2.0 g and containing a concentration, by weight, of 79.77% CBDA and 1.6% total THC. The product collapsed into an oil when warmed.

Although a combination of features is shown in the illustrated examples, not all of them need to be combined to realize the benefits of various embodiments of this disclosure. In other words, a system designed according to an embodiment of this disclosure will not necessarily include all of the features shown in any one of the Figures or all of the portions schematically shown in the Figures. Moreover, selected features of one example embodiment may be combined with selected features of other example embodiments.

The preceding description is exemplary rather than limiting in nature. Variations and modifications to the disclosed examples may become apparent to those skilled in the art that do not necessarily depart from this disclosure. The scope of legal protection given to this disclosure can only be determined by studying the following claims.

What is claimed is:

1. A method for chemical separation of cannabinoids, the method comprising:
   i) providing a starting organic solvent solution that contains a mixture of cannabinoid acids;
   ii) using an aqueous basic solution to remove a portion of the cannabinoid acids from the mixture of cannabinoid acids in the starting organic solvent solution by converting the portion of the cannabinoid acids to cannabinoid carboxylate salts that solubilize in the aqueous basic solution;

iii) separating the aqueous basic solution in (ii) from the starting organic solvent;
iv) combining the aqueous solution from (iii) with new organic solvent to produce a combined solution;
v) acidifying the combined solution to extract the cannabinoid acids from the aqueous solution to the organic solvent;
vi) separating the organic solvent of (v) from the aqueous solution; and
vii) evaporating the organic solvent of (vi) to leave product cannabinoid acids.

2. The method as recited in claim 1, wherein the starting organic solvent solution includes a non-polar solvent and a polar solvent.

3. The method as recited in claim 2, wherein the non-polar solvent is hexane and the polar solvent is ethyl acetate.

4. The method as recited in claim 1, wherein the aqueous basic solution of (ii) is aqueous sodium hydroxide.

5. The method as recited in claim 4, wherein the aqueous sodium hydroxide is at least 1 M.

6. The method as recited in claim 1, wherein the separating in (iii) and in (vi) are conducted using a separatory funnel.

7. The method as recited in claim 1, wherein the organic solvent of (iv) includes a non-polar solvent and a polar solvent.

8. The method as recited in claim 1, wherein the acidifying includes adding an acid to the combined solution until the combined solution has a pH of less than 5.

9. The method as recited in claim 8, wherein the acid is hydrochloric acid.

10. The method as recited in claim 1, further comprising desiccating the organic solvent of (vi) to remove acid.

11. The method as recited in claim 10, further comprising, following the desiccating, filtering the organic solvent.

12. The method as recited in claim 11, wherein the product has, by weight, a concentration of less than 0.3% of tetrahydrocannabinolic acid (THCA).

13. The method as recited in claim 12, wherein the product has, by weight, a concentration of at least 80% of cannabidiolic acid (CBDA).

14. A method for chemical separation of cannabinoids, the method comprising:
providing a starting cannabis material that contains cannabinoids, including, by weight, a concentration of more than 0.3% of total tetrahydrocannabinol;
i) combining the starting cannabis material with an organic solvent to produce a starting organic solvent solution that contains cannabinoid acids;
ii) using an aqueous basic solution to remove a portion of the cannabinoid acids from the starting organic solvent solution by converting the cannabinoid acids to cannabinoid carboxylate salts that solubilize in the an aqueous basic solution;
iii) separating the aqueous basic solution in (ii) from the starting organic solvent solution, the separated aqueous basic solution including a lower concentration of total tetrahydrocannabinol than the starting cannabis material;
iv) combing the aqueous basic solution of (iii) with fresh organic solvent to remove a portion of the cannabinoid acids from the aqueous basic solution, separating the aqueous basic solution in from the organic solvent, the separated aqueous basic solution including a lower concentration of total tetrahydrocannabinol than the aqueous basic solution of (iii), and combining the separated aqueous solution from with fresh organic solvent to form a combined solution;
v) acidifying the combined solution to extract cannabinoid acids from the aqueous solution to the organic solvent;
vi) separating the organic solvent of (v) from the aqueous solution; and
vii) evaporating the organic solvent of (vi) to leave a purified form of the cannabinoid acids, the purified form having, by weight, a greater concentration of the total tetrahydrocannabinol than the starting cannabis material.

15. The method as recited in claim 14, wherein the starting cannabis material includes cannabis plant matter.

16. The method as recited in claim 14, wherein the organic solvent includes a non-polar solvent.

17. The method as recited in claim 16, wherein the aqueous basic solution of is aqueous sodium hydroxide.

18. The method as recited in claim 17, wherein the separating in (iv) and in (vi) are conducted using a separatory funnel.

19. The method as recited in claim 18, wherein the acidifying includes adding hydrochloric acid to the combined solution until the combined solution has a pH of less than 5.

20. The method as recited in claim 14, wherein the purified form has, by weight, a concentration of at least 80% of a combined amount of tetrahydrocannabinolic acid (THCA) and cannabidiolic acid (CBDA).

* * * * *